(12) United States Patent
Vilsmeier

(10) Patent No.: US 7,558,617 B2
(45) Date of Patent: *Jul. 7, 2009

(54) NEURO-NAVIGATION SYSTEM

(75) Inventor: Stefan Vilsmeier, Poing (DE)

(73) Assignee: BrainLAB AG, Feldkirchen (DE)

( * ) Notice: Subject to any disclaimer, the term of this patent is extended or adjusted under 35 U.S.C. 154(b) by 798 days.

This patent is subject to a terminal disclaimer.

(21) Appl. No.: 11/060,952

(22) Filed: Feb. 18, 2005

(65) Prior Publication Data

US 2005/0203374 A1 Sep. 15, 2005

Related U.S. Application Data

(60) Division of application No. 10/083,041, filed on Feb. 26, 2002, now Pat. No. 6,859,660, which is a division of application No. 09/695,130, filed on Oct. 24, 2000, now abandoned, which is a division of application No. 08/919,454, filed on Aug. 28, 1997, now Pat. No. 6,351,659, which is a continuation-in-part of application No. 08/713,212, filed on Sep. 12, 1996, now Pat. No. 5,769,861.

(30) Foreign Application Priority Data

Sep. 28, 1995 (DE) ............................... 195 36 180
Sep. 26, 1996 (DE) ............................... 196 39 615

(51) Int. Cl.
*A61B 5/05* (2006.01)
(52) U.S. Cl. ...................................... 600/426; 600/407
(58) Field of Classification Search ................ 600/407, 600/410, 414, 417, 424, 426
See application file for complete search history.

(56) References Cited

U.S. PATENT DOCUMENTS

| | | | |
|---|---|---|---|
| 4,722,056 A | 1/1988 | Roberts et al. |
| 4,791,934 A | 12/1988 | Brunnett |
| 4,860,331 A | 8/1989 | Williams et al. |
| 4,896,673 A | 1/1990 | Rose et al. |
| 4,955,891 A | 9/1990 | Carol |
| 5,197,476 A | 3/1993 | Nowacki et al. |
| 5,230,338 A | 7/1993 | Allen et al. |
| 5,249,581 A | 10/1993 | Horbal et al. |
| 5,251,127 A | 10/1993 | Raab |
| 5,295,483 A | 3/1994 | Nowacki et al. |
| 5,305,203 A | 4/1994 | Raab |
| 5,309,913 A | 5/1994 | Kormos et al. |
| 5,315,630 A | 5/1994 | Sturm et al. |
| 5,320,462 A | 6/1994 | Johansson et al. |

(Continued)

*Primary Examiner*—Long V Le
*Assistant Examiner*—Saurel J Selkin
(74) *Attorney, Agent, or Firm*—Renner, Otto, Boisselle & Sklar, LLP

(57) ABSTRACT

The invention relates to a Neuro-navigation system comprising a reflector referencing system including passive reflectors and a marker system with markers or landmarks wherein the reflectors as well as the markers as regards their shape, size and material selection as well as their arrangement or attachment on the parts of the body to be operatively treated and on the surgical instruments are configured so that mapping their locations is substantially facilitated or is able to take place more accurately positioned by a computer/camera unit having a graphic display terminal as well as the operative treatment with the aid of this unit. Optionally a surgical microscope, an ultrasonic diagnostic system as well as a calibration procedure may be integrated in the Neuro-navigation system in accordance with the invention.

12 Claims, 2 Drawing Sheets

U.S. PATENT DOCUMENTS

| | | |
|---|---|---|
| 5,383,454 A | 1/1995 | Bucholz |
| 5,389,101 A | 2/1995 | Heilbrun et al. |
| 5,394,457 A | 2/1995 | Leibinger et al. |
| 5,394,875 A | 3/1995 | Lewis et al. |
| 5,397,329 A | 3/1995 | Allen |
| 5,411,026 A | 5/1995 | Carol |
| 5,446,548 A | 8/1995 | Gerig et al. |
| 5,494,034 A | 2/1996 | Schlöndorff et al. |
| 5,551,429 A | 9/1996 | Fitzpatrick et al. |
| 5,588,430 A | 12/1996 | Bova et al. |
| 5,603,318 A | 2/1997 | Heilbrun et al. |
| 5,617,857 A | 4/1997 | Chader et al. |
| 5,622,170 A | 4/1997 | Schulz |
| 5,630,422 A | 5/1997 | Zanakis |
| 5,630,431 A | 5/1997 | Taylor |
| 5,643,268 A | 7/1997 | Vilsmeier et al. |
| 5,662,111 A | 9/1997 | Cosman |
| 5,676,673 A | 10/1997 | Ferre et al. |
| 5,681,326 A | 10/1997 | Lax |
| 5,682,890 A | 11/1997 | Kormos et al. |
| 5,695,500 A | 12/1997 | Taylor et al. |
| 5,695,501 A | 12/1997 | Carol et al. |
| 5,704,897 A | 1/1998 | Truppe |
| 5,748,767 A | 5/1998 | Raab |
| 5,755,725 A | 5/1998 | Druais |
| 5,769,861 A | 6/1998 | Vilsmeier |
| 5,772,594 A | 6/1998 | Barrick |
| 5,836,954 A | 11/1998 | Heilbrun et al. |
| 5,851,183 A | 12/1998 | Bucholz |
| 5,921,992 A | 7/1999 | Costales et al. |
| 6,006,126 A | 12/1999 | Cosman |

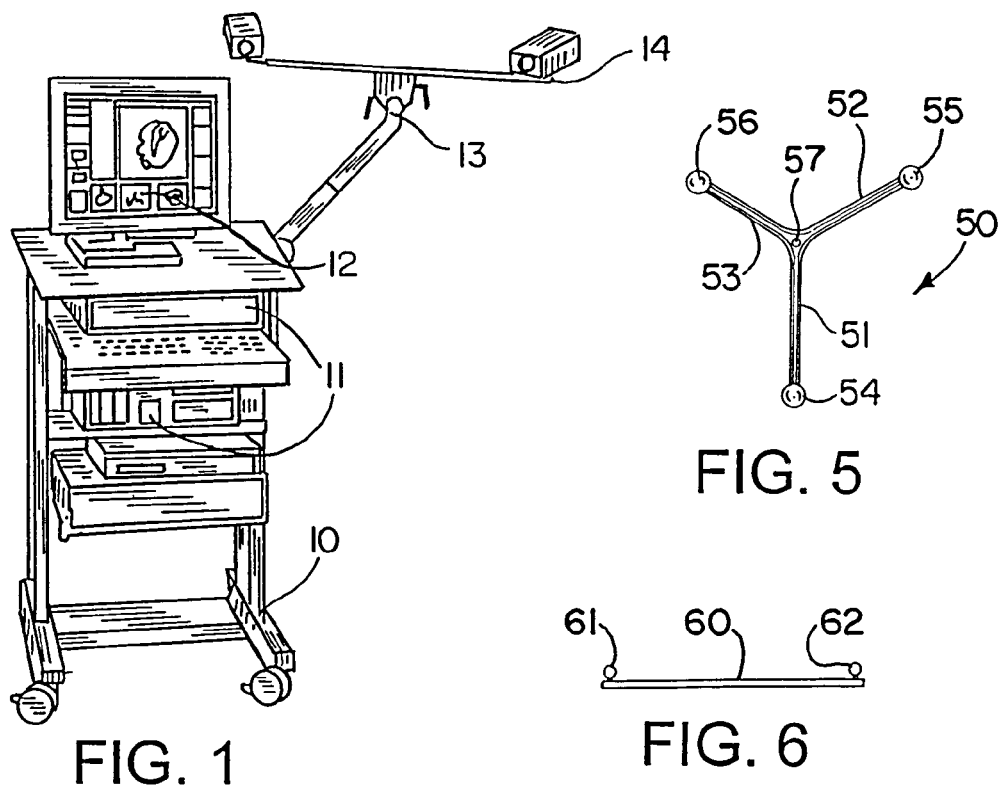
FIG. 1
FIG. 5
FIG. 6
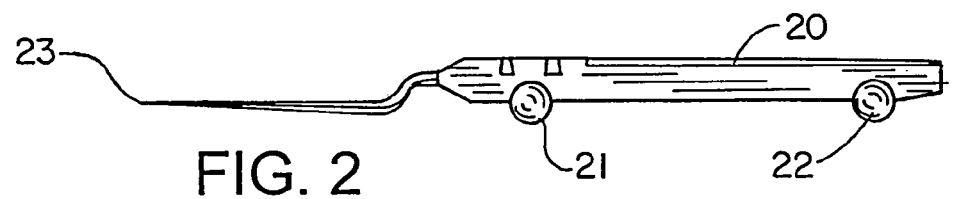
FIG. 2
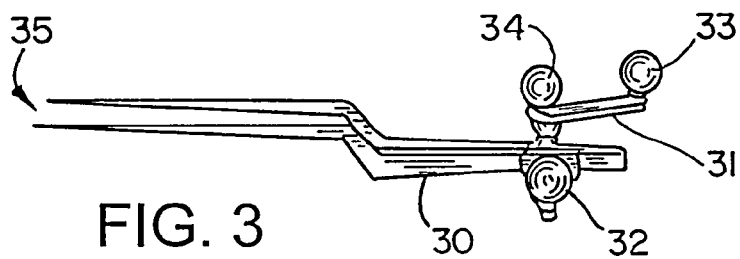
FIG. 3
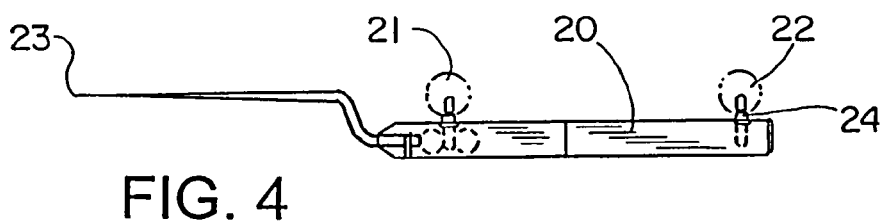
FIG. 4

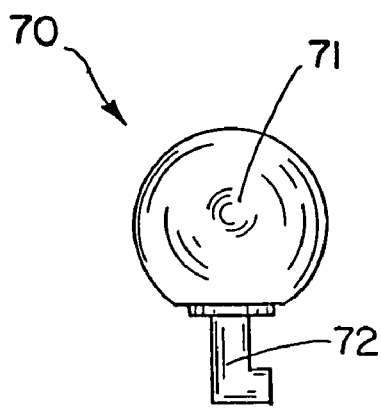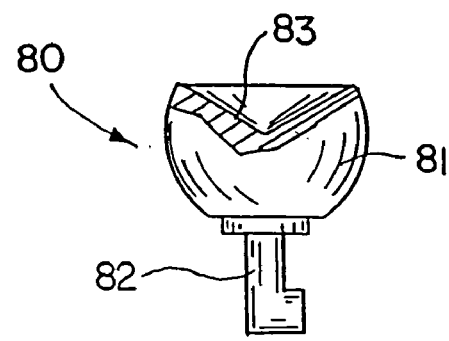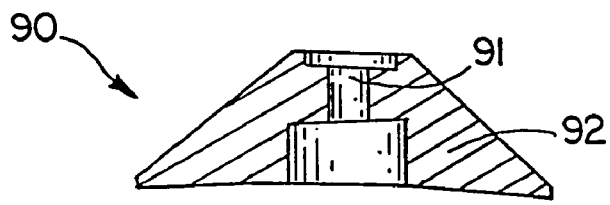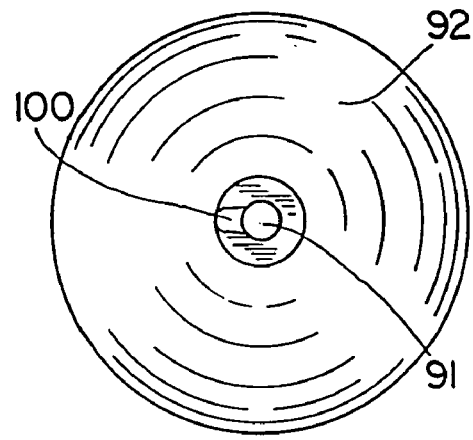

NEURO-NAVIGATION SYSTEM

This application is a divisional of U.S. patent application Ser. No. 10/083,041 filed on Feb. 26, 2002 now U.S. Pat. No. 6,859,660 which is a divisional of U.S. patent application Ser. No. 09/695,130 filed Oct. 24, 2000 now abandoned, which is a divisional of Ser. No. 08/919,454 filed Aug. 28,1997 now U.S. Pat. No. 6,351,659, which is a continuation in part of Ser. No. 08/713,212 filed Sep. 12, 1996 now U.S. Pat. No. 5,769,861, all of which are hereby incorporated herein by reference in their entirety.

BACKGROUND OF THE INVENTION

1. Field of the Invention

The invention relates to a neuro-navigation system comprising a reflector referencing system including passive reflectors and a marker system with markers or landmarks wherein the reflectors as well as the markers as regards their shape, size and material selection as well as their arrangement or attachment on the parts of the body to be operatively treated and on the surgical instruments are configured so that mapping their locations is substantially facilitated or is able to take place more accurately positioned by a computer/camera unit having a graphic display terminal as well as the operative treatment with the aid of this unit. Optionally a surgical microscope, an ultrasonic diagnostic system as well as a calibration procedure may be integrated in the Neuro-navigation system in accordance with the invention.

2. Description of the Prior Art

Neuro-navigation systems represent the link between the surgeon carrying out the operation, i.e. the anatomy of the patient as seen by the surgeon for operative treatment and diagnostic data furnished, for example, by computer tomography and visually displayed by the display terminal of a computer unit.

To produce this link, i.e. to render the momentary positional data of the anatomy of the patient and that of the surgical instruments and apparatus employed in the operation visible on the display terminal of the computer, devices need to be made available which are capable of mapping the position of the patient and thus the precise location of the parts of the body to be operatively treated as well as the location of the surgical instruments and, more particularly, the tips thereof in a starting position and to keep track of them during the operation.

For this purpose conventionally a computer unit is made available, to which two or more referencing cameras are connected. With these cameras both the position of artificial or natural landmarks affixed to the patient as well as the position of radiative emitters applied to the surgical instruments are mapped.

The procedure as regards the landmarks affixed to the patient on systems hitherto is as follows:

Prior to implementing computer tomography a set of artificial landmarks is affixed to the patient surrounding the zone to be operatively treated. These landmarks which can be mapped by the cameras in both the computer tomography as well as later in the operation are totally identical to each other, they being affixed to the patient by sticky plaster, for example.

After this treatment the data of the computer tomography, i.e. both the positional data of the artificial landmarks each identical to the other and the position of the operation target and the surrounding areas are entered into the computer system which together with the referencing or mapping cameras is arranged on the operating table. This is followed by a time-consuming step in which the surgeon needs to access the individual landmarks on the patient with a pointer, he then having to enter into the computer which of the identical landmarks in the operating position correspond to those sensed in the computer tomography. For this purpose all landmarks need to be accessed a number of times, followed each time by the time-consuming manual assignment to the computer tomography (CT) data. Since the landmarks secured by sticky plaster fail to comprise characteristical reference points, which cannot be missed in accessing them with an instrument tip, mapping in this respect can only take place relatively inaccurately.

A further disadvantage in this respect is that the conventional landmarks, once covered with sterile cloths, are no longer directly discernible, because of their flat configuration, and thus can no longer be accessed precisely in position should the patient already be covered. This causes problems particularly later on when the position of the patient is changed during the operation and the landmarks need to be reaccessed with the pointer for a readjustment.

Furthermore, it is a disadvantage that the known landmarks, once affixed to the patient, are no longer removable by being able to be replaced by other landmarks in precisely the same position.

Conventional emitter systems for surgical instruments and apparatus employed in the operation are configured as follows:

Two or more active emitters, emitting, for example, beams of infrared radiation, are applied to each instrument or operation apparatus and act as spot emitters located on a surface area. In the instrument an electronic device is provided permitting emission of the signals, the instrument being connected at its rear end by a cable to the computer unit. Due to the emitted signals the computer unit is able to identify the three-dimensional position of the instruments or the tips thereof.

This conventional instrument referencing system is also hampered by several drawbacks as explained in the following. Using active, i.e. self-emitting signal transmitters already has the disadvantage that electronic means need to be provided in the instruments which makes particularly the manufacture of such instruments more expensive. In addition, the cables attached to each instrument connecting it to the computer unit are an obstruction to movement and can get in the way during the operative treatment due to the many instruments often to be used.

The emitters attached as points to a surface area of the instrument can be "seen" only in a very restricted angular viewing range of the camera system, i.e. they may easily be concealed by the instrument itself or by the hand of the surgeon.

Sterilization of such instruments can only be done by gas sterilization. Such a gas sterilization may last up to a whole day, as a result of which several sets of instruments need to be purchased to ensure that sterilized instruments are available for operative treatment at all times when often required.

One serious drawback of the conventional referencing system is that the surgeon is only able to use exclusively the instruments made available by the system manufacturer. Many surgeons are, however, used to their own set of instruments and need to adapt when using another specified set of instruments which may have a negative effect on the outcome of the operation.

It is a disadvantage that conventional Neuro-navigation systems fail to provide a simple calibration system with which the angles or spacing of the mapping or referencing cameras can be mapped or recalibrated at any time without complication. Since these cameras are often subject to a change in position during the operation due to, for example, one of the persons carrying out the operative treatment jolting the camera stand, speedy and easy recalibration during the operation is of major importance.

In a neurosurgical operation it is often the case that a surgical microscope is used. Such microscopes are conventionally mounted on a heavy base and frame, the actual microscope as such being secured to the end of an articulated arm permitting powered and manual positional shifting of the microscope and signalling the positional data, for example, in sensing the angular position of the arm joints for feedback to a computer unit used in Neuro-navigation.

The bases or stands of such microscopes need to be configured very heavy and safe-standing to prevent, for instance, jolting the microscope from possibly changing its position, thus ruining Neuro-navigation of the microscope calibrated at the outset to the starting position. Microscopes are namely conventionally unable to output any additional position feedback signals to the Neuro-navigation computer other than the positional data resulting from the position of the arm.

In conclusion, it is often the case in neurosurgical operations that ultrasonic diagnostic systems, as known, for instance, in examination during a pregnancy, find application. It has hitherto been a drawback in the case of conventional systems that although the position of the sensed parts of the body could be related to the ultrasonic emitter and detector, there was no possibility of simply assigning this data to a Neuro-navigation system made available on the operating table.

SUMMARY OF THE INVENTION

It is thus the object of the present invention to provide a Neuro-navigation system which overcomes the cited drawbacks of prior art by, more particularly, substantially facilitating mapping the locations of surgical instruments and apparatus employed in the operation as well as referencing the anatomy of the patient and the operation apparatus with the aid of the Neuro-navigation system in accordance with the invention or with more accurate positioning. It is furthermore intended to make it possible to integrate a surgical microscope, an ultrasonic diagnostic system as well as a procedure for calibrating the camera position in a Neuro-navigation system.

This object is achieved by the subject matters of the independent claims. Advantageous embodiments are defined by the sub-claims.

The referencing system in accordance with the invention operates with passive reflectors instead of prior art active signal emitters, this referencing system being employed for neurosurgical instruments and apparatus employed in the operation. More particularly, this involves the application of a source of preferably infrared radiation, at least two mapping or referencing cameras and a computer unit with a graphic display terminal connected to the cameras. In accordance with the invention the reflector referencing system comprises at least two reflectors which can be applied replaceable via adapters to instruments or apparatus employed in the operation, i.e. in an arrangement which is exclusively characteristical for this array of reflectors. The special advantage of such a referencing system employing passive signal transmitters, i.e. reflectors, is that due to the characteristical individual arrangement of the reflectors each surgical instrument reflects an image which can be sensed characteristically exclusive for the particular instrument concerned, this being the reason why the computer unit immediately "recognizes" each individual instrument via the camera sensing and is able to explicitly display the position of its tip, for example.

Since passive, i.e. reflective, emitters are used, a cable connection to the computer unit as well as an electronic "internal life" of the instruments is no longer necessary, thus giving the surgeon more freedom of movement due to obstructions by cables being eliminated.

The reflectors which can be removably attached preferably via adapters to the instruments or apparatus employed in the operation open up the possibility of carrying out an autoclave steriliztion of the instruments once the reflectors have been removed. Unlike prior art gas sterilization such an autoclave sterilization can be carried out in much shorter time (roughly 20 min.), thus merely making it necessary to provide one or more sets of sterilized reflectors for attachment to the instruments sterilized in autoclave sterilization, i.e. there no longer being a need to provide several complete sets of instruments as in prior art.

The reflectors to be removably attached via adapters to the surgical instruments can be positioned at a certain spacing away from the attachment surface area, as a result of which a much greater angular range materializes, as compared to conventional systems, in which the reflectors can still be viewed by the camera system.

In one advantageous aspect of the reflector referencing system in accordance with the invention the reflectors are configured spherical and provided with a reflective coating, balls of this kind emitting a uniform reflection image as viewed from all directions in space.

It is advantageous when two of the reflectors in accordance with the invention are secured to an instrument, more particularly, to connectors attached to a pointer or a calibration rod. Such connectors permit the reflectors to be attached and removed easily and positionally exact. The spacings of the two reflectors are established by the positions of the connectors characteristical for each instrument permitting the latter to be tracked and identified by the navigation system in every phase of the operation.

In a further aspect of the referencing system three reflectors are secured to at least one arm end of an adapter configured by three reflector arms and a fastener base in each case, the fastener base being securable to a surgical instrument or an operation apparatus. In turn the three reflectors attached to the arm ends of the adapter are provided in a characteristical arrangement, i.e. for each adapter the angular position of the arms as well as their length, for example, is individually unique as a result of which a characteristic reflection image for each adapter materializes. The great advantage of this configuration is that such an array of reflectors can be secured to practically any surgical instrument by its adapter via the fastener base. This opens up the possibility for the surgeon to continue to employ the instruments to which he is used to, i.e. to incorporate them in the Neuro-navigation system. All that is needed for this is a brief calibration to a reference adapter, described later, to teach the system the position of the tip of the surgical instrument. This adapter system too simplifies sterilizing the instruments in the way as already described. The system provides a sufficient number of adapters having characteristic arrays of reflectors so that all necessary instruments can be put to use with the Neuro-navigation system.

The aforementioned reference adapter is made available in accordance with a further advantageous embodiment of the present invention, it likewise comprising a fastener base having three reflectors securable in a particularly characteristic arrangement to the end of three arms, the base being provided at its end with a clamping device adapting flexibly to the fastening position in each case.

This reference adapter has, more particularly, two functions. For one thing it can be secured to a point firmly connected to the operating table, for example, to the device for holding the part of the body to be operatively treated. As a result of this and due to the fact that the computer unit assigns the characteristic image exclusively to this reference adapter, this ensures that positionally accurate referencing of all anatomical data of the patient as well as a reflection pattern which is fixed relative to the patient is still made possible even when it is necessary during the operation to shift or tilt the operating table or should its position be accidentally changed by it being jolted. The reflection of the reference adapter signals the position of the system part firmly connected to the patient to the computer unit at all times so that no inaccuracies and no collapse of the navigation can occur due to such changes.

The clamp on the fastener base of the reference adapter may be configured in various ways, for instance, it being configured with a screw clamp for attachment to a retaining device, whilst in the case of it being attached to a bone part, soft and positionally flexible clamp ends may be used to avoid damage of bone tissue, this latter possibility being useful, more particularly, in the case of an invasion in the spinal region where the reference adapter is secured, for example, to extensions of the vertebrae.

In another aspect of the reference adapter it features preferably at the starting point of the three arms a conically tapered funnel having a central calibration point for the tips of the surgical instruments, this being the case in which the second function of the reference adapter is useful. As already explained, the reference adapter characterizes in the navigation system a point which is fixed in relation to the patient. This property can be made use of by a calibration point being simultaneously assigned to the reference adapter with the aid of which the tip positions of the surgical instruments can be mapped. As to be explained later use can also be made of this calibration point in mapping the three-dimensional positions of other apparatus.

Surgical instruments, more particularly, instruments which the surgeon has been used to for a long time, can be fitted, as already described, with a triple reflector adapter which then provides a characteristic reflection image of the instrument concerned. For this purpose, however, the navigation system needs to be informed of where the tip is located, use being of the calibration point on the reference adapter for this purpose. The surgeon applies the tip of his instrument to the calibration point known in location, this being facilitated by the funnel of the bowl conically tapered to this point, the tip also being established by it being located absolutely motionless. The surgeon then executes a few spatial movements with the end of the instrument to which the triple reflector adapter is secured. In this movement, since the tip of the instrument is motionless, each reflector covers a distance which is located on a spherical surface area at the perpendicular spacing of the reflector away from the centerpoint of the funnel. The computer unit of the navigation system is able to identify this special movement and "recognizes" that with this triple reflector adapter a tip calibration has just been made, it then computing the spacing of the tip away from the reflector in each case and thus the tip position of the surgical instrument and assigning it to the characteristic reflection pattern of the three reflectors applied to the instrument. The instrument is thus calibrated and explicitly identified, i.e. it can be put to use throughout the complete operation.

The marker system for referencing and mapping parts of the body to be operatively treated neurosurgically comprises at least three artificial landmarks and just as many devices for attaching the landmarks to the patient. In accordance with the invention each individual landmark provides a unique image characteristic both for mapping the diagnostic data of the patient and for subsequently monitoring the operation.

As compared to prior art which, as already mentioned, works with landmarks affixed by e.g. sticky plasters, the marker system in accordance with the invention features the following advantages:

The landmarks can be identified individually, i.e. both during the computertomography and by the Neuro-navigation system during the operation. The individually mapped landmarks are assigned to only one position in the three-dimensional coordinate system, i.e. there is no possibility of the cameras confusing the landmarks when being mapped by the Neuro-navigation system.

Due to this configuration there is now no need for the troublesome first step in referencing the patient as required by prior art. Although the surgeon still needs to access at least three landmarks individually there is now, however, no need to manually assign the positions for these landmarks in each case since the Neuro-navigation system "recognizes" the reflection of the accessed landmark and assigns its position exclusively to that of the landmark mapped in the computer tomography having the same characteristic image, thus saving the complete time needed for landmark assignment. Since the three-dimensional arrangement of the landmarks relative to each other also produces a characteristic image in the Neuro-navigation system, it is usually sufficient to access three landmarks with a pointer, the tip position of which is known to the system, for example, by an aforementioned reflector arrangement to implement a sufficiently accurate referencing of the anatomical data of the patient. The marker system in accordance with the invention thus permits to advantage a very much quicker and more accurate mapping and referencing of parts of the body to be operatively treated by neurosurgery.

The aforementioned landmarks may consist of metal bodies which due to their specific material density, size, shape and arrangement relative to each other can be individually distinguished in data acquisition in a computer tomography as well as in mapping with infrared cameras. Preferably, these landmarks consist of aluminum bodies of a specific shape or size removable from their fasteners. Such aluminum bodies are simple to manufacture and easy to map due to their metallic nature. In addition, they are relatively lightweight and thus do not detach by their own weight the fasteners, to which they are releasably secured, from the patient. The two-part arrangement of the landmarks also plays an important role. The fasteners, affixed to the skin of the patient, for example, by an adhesive applied to the base part, may be configured somewhat prominently, for instance, as a base to which the corresponding landmark can be secured by means of a connection or some other kind of quick-release, fastener, thus making it basically possible to swap the landmarks for implementing special setting procedures. Furthermore, the complete marker with its fastener base and mounted landmark protrudes sufficiently far from the patient so that it can still be simply located even when hidden by sterilizing cloths.

The marker system in accordance with the invention is supplemented in a particularly preferable embodiment thereof by it comprising an additional set of funnel-shaped landmarks, the funnel centerpoint of which corresponds to the centerpoint of the landmarks for which they can be swapped prior to referencing on the operating table.

By supplementing the marker system in this way the accuracy of mapping and referencing the anatomy of the patient can be enhanced to a significant degree. The landmarks employed in the computer tomography are removed from the fasteners on the patient after the computer tomography and replaced by landmarks which feature a means having a tapered internal funnel by means of which the centerpoint or starting point thereof is positioned precisely at the center of the landmark, so that the tip of the surgical instrument can be applied precisely in position in referencing and is unable to be shifted out of place.

Should, for example, the landmark as used in the computer tomography be a ball having a certain diameter, this can be replaced after the computer tomography by e.g. a three-quarter ball of the same diameter having at its upper section a funnel which tapers precisely to the centerpoint of the ball. Due to its diameter being in agreement the three-quarter ball is still identifiable as being the same landmark as the complete ball which it replaced.

In the step of identifying the landmark as described above, the surgeon can now access precisely the centerpoint of the landmark with the pointer. As a result of this, inaccuracies in accessing the point, as may result in the system as compared to prior art, the landmarks of which fail to provide any prominent points, can be avoided very well, i.e. referencing and mapping the landmark centerpoint now being implemented with excellent precision. In this referencing procedure too, the same as in the calibration procedure by means of the calibration point of the reference adapter as explained above, the tip of the pointer can be maintained at one position whilst its end is moved. In referencing each landmark the computer unit is informed by the tip being motionless whilst the pointer is moved that at this time a landmark referencing procedure is being done.

This "funnel configuration" is furthermore of advantage when the landmarks need to be re-referenced for some reason during the operation. When namely the patient has already been covered by sterile cloths and the landmarks are under these cloths they can still be well identified due to their prominent structure. Due to the configured funnel shape and because the sterilization cloths are relatively thin the centerpoint of the landmarks can now also be accessed very accurately even though the landmarks are already covered by cloths, i.e. there is no longer a need to uncover the patient should referencing need to be repeated and recovered after referencing which is never possible in actual practice.

The invention comprises furthermore a calibration procedure for mapping the angles and spacings of referencing cameras in which a calibration tool having two reflectors applied at predetermined positions at a known spacing are incorporated in the viewing range of both cameras, the calibration tool being moved three-dimensionally in the viewing range, several intermediate positions of the calibration tool being imaged by the referencing cameras and converted by means of a computer unit individually into three-dimensional coordinates and the computer unit computing and memorizing the angular and spacing positions of the cameras from the three-dimensional positions of the reflectors.

The possibility of the camera stand or the cameras themselves being jolted by a participant in the operation can never be completely excluded. Such a change in position of the cameras during the operation may, however, result in different images suddenly being furnished to the computer system. For undertaking a recalibration, taking up little time, but also for implementing an initial calibration, the procedure as described above in accordance with the invention offers an advantageous possibility since the computer unit knows the shape of the reflectors and their spacing away from the calibration tool and is thus able to "recognize" in a separate camera setting calibration step of this calibration tool when the latter is swivelled into the viewing range of the cameras.

The information resulting from "snap shots" of several positions of the calibration tool during its movement enable the computer unit to deduce the camera position from the known data of the calibration tool, i.e. in but a short time the computer unit is able to "recognize" the camera position. This procedure saves time firstly in the initial setting and is secondly well suited also for readjusting following a change in camera position due to it being speedy and simple to implement.

In a three-dimensional movement of the calibration tool in calibrating the cameras it is of advantage when both reflectors are spaced away from each other as far as possible at all times, i.e. relative to the projected camera mapping plane. This is why in an advantageous aspect of the calibration procedure the three-dimensional movement of the calibration tool and thus of the reflectors is displayed throughout on a graphic display terminal, for example, the monitor of the Neuro-navigation system. The movements can then be implemented so that both reference points are spaced away from each other as far as possible on the display in enhancing the speed and accuracy of the calibration.

A pointer provided with removable reflectors may be used to advantageous as the calibration tool, this pointer being needed in any case for each operation. The data of the reflectors as well as their spacing are then input into the system as the data of the calibration tool.

As an alternative there is the possibility of employing a separate calibration rod provided with removable reflectors, this calibration rod then being employed each time associated with the system concerned. Advantageously such a calibration rod may be longer than a pointer, for example. In this way too, the speed and accuracy of the calibration can also be improved.

The invention relates furthermore to a control for a surgical microscope, this microscope comprising the following components:

a microscope stand having a base and several articulated arms movable on each other three-dimensionally powered or manually, and a microscope mounting or control unit, a source of preferably infrared radiation, at least two mapping or referencing cameras, and a computer unit and graphic display terminal connected to the cameras.

In accordance with the invention the microscope is characterized by at least three reflectors being applied thereto removably via an adapter in an arrangement characteristic exclusively for this reflector array.

As mentioned at the outset, the drawback of prior art microscopes is that these are only able to feed back their position signal to the computer unit of a Neuro-navigation system relative to the angle setting of the carrier arm parts, this being the reason why they need to be fitted with very heavy stands and bases so that no accidental shift in the position of the microscope could result in Neuro-navigation losing reference and having to be discontinued.

The microscope control in accordance with the invention comprising a characteristic reflector arrangement adapted on the microscope now offers the possibility of a further feedback of microscope mapping data. Due to the special arrangement of the reflectors a Neuro-navigation system is able to identify this arrangement as a microscope reflector arrangement at any time. The microscope position is thus signalled via the camera system to the computer directly as a three-dimensional position. Accordingly, even if the microscope is jolted, the data from the arm joint position and that of the reflector position can be compensated at any time, i.e. Neuro-navigation remains intact even if the microscope is jolted in position.

Three-dimensionally positioning the microscope is done to advantage in a first calibration by focusing the optics of the microscope on a point having known three-dimensional coordinates, preferably the calibration point of a reference adapter, the focusing data being transferred to the computer unit by a data transfer means whilst the same computer unit establishes the three-dimensional position of the microscope by means of the reflectors and cameras.

In this case, use is again made of the aforementioned calibration function of a reference adapter which is likewise provided with a triple reflector arrangement. To signal the computer unit where the microscope is located in a starting position the microscope can be focused to the centerpoint of the funnel of a reference adapter as described above. The computer then receives data as to the zoom factor and the focal spacing via data transfer means, for example, a data line, from the microscope and thus "recognizes"—because the three-dimensional location of the calibration point is known—the position of the focal point as well as the microscope position from the reflection points of the reflectors applied to the microscope. From this data precise mapping of the microscope is possible.

After the first calibration there is now the possibility in accordance with the invention—by signalling the motors for moving the microscope by the computer unit or by feedback of the microscope movements and mapping data thereof to the computer unit—to carry out the following control sequences:

a) automatically tracking and focusing an instrument tip, the position of which is known to the computer unit via reflectors;

b) automatically focusing a memorized and predetermined point of operative treatment, and c) focusing a point of operative treatment from various three-dimensional and angular positions of the microscope, thus enabling the following activities to be implemented: the surgeon points the tip of a pointer provided with reflectors known to the navigation system at a location of the part to be operatively treated, the computer unit thereby identifying the coordinates of this position and running the microscope to this position and precisely adjusting the focus to this position. This saves the surgeon having to do the complicated manoevering tasks with the microscope control system. The surgeon is also able to supply the system with a certain point which he has already focused, for memorizing. This point can afterwards be refocussed by the microscope at any time when simply commanded. Sometimes, particularly when focusing needs to be done within cavities having only small openings, the imaginary line of focus of the microscope must be "jiggled" about this opening to "illuminate" the cavity as a whole. By means of the present control there is likewise the possibility of memorizing the point of concentration of this line and to undertake an illumination as described before.

Furthermore, in accordance with the invention an ultrasonic diagnostic system including a ultrasonic emitter/detector and an analyzer and a display connected thereto is defined. This system is characterized in accordance with the invention by a reflector adapter having at least three reflectors being secured to the ultrasonic emitter/detector, this reflector adapter being integrated in a reflector referencing system as described at the outset.

With such an aspect in accordance with the invention data received by an ultrasonic diagnostic unit can now be mapped in a Neuro-navigation system. The ultrasonic emitter/detector also features an array of reflectors in a special arrangement identified by the computer as being unique thereto. When the data established by the ultrasound system is calibrated with the anatomy data from the computer tomography this system also obviates the difficulties which could possibly otherwise materialize by the tissue to be operatively treated "collapsing" somewhat after an opening has been made in the layers of tissue located above the area of operative treatment.

In all the Neuro-navigation system in accordance with the invention comprises several components, namely a reflector referencing system, a marker system, a calibration procedure for the cameras, a microscope control and an ultrasonic diagnostic system. It will be appreciated that all of these parts of the system may be each put to use and achieved separately whilst being useful in any combination thereof in bringing the advantages as described above over prior art to effect.

BRIEF DESCRIPTION OF THE DRAWINGS

The invention will now be described in more detail by way of an example with reference to the drawing in which:

FIG. 1 illustrates a frame in which a computer unit with a keyboard is accommodated, on which a computer monitor as the graphic display terminal stands and to which a camera mount with two infrared cameras is attached;

FIG. 2 illustrates a neurosurgical pointer having reflectors in accordance with the invention attached thereto;

FIG. 3 illustrates a surgical pincette, to the rear end of which an adapter having three reflectors in a special arrangement is secured;

FIG. 4 is a cross-section through a pointer provided with two reflectors;

FIG. 5 is a plan view of a reference adapter having three reflectors and a calibration point;

FIG. 6 illustrates a calibration rod on a smaller scale;

FIG. 7 illustrates a landmark prominence as used in producing a computer tomograph;

FIG. 8 illustrates a landmark prominence as used in referencing landmarks on the operating table;

FIG. 9 is a cross-section through a base for securing the landmark prominences as shown in FIGS. 7 and 8; and FIG. 10 is a plan view of the fastener base shown in FIG. 9.

DESCRIPTION OF THE PREFERRED EMBODIMENTS

In an operating theater in which the Neuro-navigation system in accordance with the invention is put to use, a frame as identified by the reference numeral 10 in FIG. 1 stands, for example, at one end of an operating table. Accommodated in this frame is a computer unit 11 and various other control units such as, for example, a keyboard (not identified). Connected to this computer unit is the monitor 12 placed on the frame. This monitor displays in various views, also in a three-dimensional view, section planes or images of the anatomy of the patient, it also showing the positions of surgical instruments or reflectors attached to these instruments and to the operation apparatus. Additional information may be output in further fields on the screen.

Likewise secured to the upper part of the frame, on which the monitor 12 stands, is the camera mount 13. This camera mount 13 is configured adjustable and carries at the ends of its upper arms two infrared cameras, identified by 14.

The aforementioned components are, of course, interconnected by data transfer lines. The cameras 14 view the portion of the operating table where operative treatment is taking place and can map three-dimensional coordinates of surgical instruments and apparatus employed in the operation provided with reflectors which reflect infrared beams.

The head of a patient is secured firmly in place on the operating table, for example, by a locating device. The coordinates of the anatomy of the patient are initially signalled to the computer unit 11 shown in FIG. 1 by a marker system, further described in the following, by computer tomography data, the arrangement of the markers during the operation at any one time also being referenced locally with the aid of the computer unit and the cameras.

For this purpose use is made of the pointer 20 shown in FIG. 2. The pointer 20 comprises two reflectors 21 and 22 applied to it by connectors. The spacing and shape of these reflectors 21 and 22 are known to the computer unit 11, i.e. this pointer 20 is always the one which is assigned to the computer system in each case. Also known to the computer unit 20 is the position of the tip 23 of the pointer 20. When this pointer 20 is brought into the viewing field of the cameras 14 it can be directly "recognized" by the system, i.e. its tip 23 can be displayed on the monitor 12.

FIG. 3 now shows a surgical pincette 30. Releasably connected to the rear end of this pincette 30 is an adapter 31 carrying on its arms three reflectors 32, 33 and 34 having a characteristical arrangement which is assigned exclusively to this adapter in the navigation system. Such a pincette 30 may be any pincette to which the adapter 31 can be applied, it may also be a pincette with which a neurosurgeon has already worked for years. To enable the pincette 30 to be put to use the Neuro-navigation system must first be informed as to the position of the pincette tip 35. For this purpose, as already described relative to the reflector referencing system, a three-dimensional point known in the navigation system is accessed by the pincette tip 35, circular movements then being implemented with the end of the pincette 30. The computer unit 11 "recognizes" via the cameras 14 the special arrangement of the reflectors 32, 33 and 34 and is able to establish the position of the tip from its movements with the tip 35 of the pincette 30 stationary.

The pointer 20 as shown in FIG. 2 as well as the pincette 30 shown in FIG. 3 are intended to represent as an example all instruments as employed in neurosurgical invasions. The system operates cordless with a reflector adapter having passive reflectors as shown in FIG. 3. These may also be secured, for example, to ultrasonic diagnostic units and neurosurgical microscopes, calibration of a microscope then being implemented, as described, by focusing a mapped calibration point.

FIG. 4 shows a section view of the pointer 20 of FIG. 2 in a different plane, clearly making it evident that the reflectors 21 and 22 are applied to the position pointer 20 by connectors. The reflectors 21, 22 are thus removable. Since the reflectors 21, 22, which are usually configured with a sensitive reflective coating, are the only parts of the position pointer 20 having a high sensitivity as regards sterilization, the position pointer 20 with the removable reflectors 21, 22 can be sterilized very easily and quickly. Once, namely, the reflectors 21, 22 have been removed an autoclave sterilization can be carried out, after which a new prepared set of sterilized reflectors 21 and 22 can be mounted. Accordingly, the position pointer 20 can thus be quickly returned to use sterilized.

FIG. 5 is a plan view of a reference adapter 50 which has already been described a number of times, and which is secured to a part fixed in location relative to the patient by a clip concealed under its centerpoint. This part may be, for example, the means for locating the head of the patient as well as a spike extension in a vertebra body.

The reference adapter 50 consists of the arms 51, 52 and 53 having a length and angular setting exclusively characteristical for this reference adapter. Secured to the end of these arms 51, 52 and 53 are the reflectors 54, 55 and 56 respectively. Due to this reflector array and its characteristic arrangement and/or size the reference adapter 50 can be explicitly identified in position at any time by the Neuro-navigation system. It is normally the case that the position of the reference adapter 50 always remains the same during the operation. Should it be necessary to change the position of the patient the reference adapter 50 connected positionally located to the referenced anatomy of the patient can also be subsequently mapped and tracked at any time by the navigation system so that the "big picture" of the patient reference system remains known to the computer unit 11 at all times.

The calibration point 57 plays a special role as regards the reference adapter 50, this calibration point being assigned to the starting point of the three arms 51, 52 and 53 in this example. The calibration point 57 is located in a bowl so that it can be precisely accessed in position by instrument tips (for example, the position pointer tip 23, FIG. 2 or the pincette tip 35, FIG. 3). After accessing, the instrument is moved, the centerpoint of which forms the tip, i.e. the bowl of the reference adapter 50 in the calibration point 57. Calibration as already described in detail can then be carried out.

Shown on a very small scale in FIG. 6 is a calibration tool, represented in this case by a calibration rod 60 which in reality should have a length of at least 40 cm or so. Reflectors 61, 62 are arranged respectively at both ends of the calibration rod 60 in a predetermined spacing known to the computer 11. The characteristic properties of the reflectors 61, 62, also configured removable in this case, namely their size as well as their spacing on the calibration rod 60, are known to the computer unit 11 which assigns them exclusively to this rod. With this rod 60 the already described calibration procedure can be carried out for setting the angle and spacing of the cameras 14.

FIG. 7 shows a landmark prominence as employed in mapping the anatomy of the patient in a computer tomograph. This prominence is identified by 70, it comprising a spherical main body 71 which, for example, is a ball of aluminum. Fitted to the bottom of this aluminum ball—which can be identified by the computer tomography as well as by the Neuro-navigation system individually due to its size being unique in the system—is a latching protrusion 72 with which the landmark prominence 70 can be inserted and latched in place in a fastener 90 (FIG. 9).

A landmark prominence by which the landmark prominence 70 shown in FIG. 7 is replaced after computer tomography is identified in FIG. 8 as landmark prominence 80. The dimensions of the main body of the landmark prominence 81, i.e. the ball diameter corresponds to those of the landmark main body 71 shown in FIG. 7. The landmark prominence 80 has been modified to the extent that an upper part of the ball has been cut off and a bowled funnel 83 machined in the ball, the tip of this funnel precisely locating the center of the ball, as is evident from the scrap view shown in FIG. 8. The latching protrusion 82 corresponds precisely to the latching protrusion 72 (FIG. 7).

Once the patient data has been mapped in the computer tomograph the landmark prominence 70 is replaced by the landmark prominence 80. Since both balls have the same diameter the landmark prominence 80 can be identified by the Neuro-navigation system as being the same landmark mapped as landmark 70 in the computer tomograph. The bowl with the funnel-tapered tip permits precisely accessing the centerpoint of the ball by the tip of the surgical instrument in referencing the landmark in the course of calibrating the Neuro-navigation system, thus making it easier and quicker to reference which can also be carried out after covering with sterile cloths.

FIG. 9 depicts a fastener 90 which is secured, for example, to the skin of the patient by means of a sticky plaster on the underside of the fastener. The base 92 of this fastener 90 comprises an insertion opening 91 into which both the landmark prominence 70 as well as the landmark prominence 80 evident from FIGS. 7 and 8 can be inserted and latched into place. FIG. 10 shows the fastener 90 as seen from above, it being evident that an additional nose-shaped opening 100 is incorporated in the base 92 through which the latching protrusions 72, 82 can be introduced. Turning the landmark prominences 70 and 80 as a whole then causes their lower protrusions to latch into place in the through-hole 91 of the base clasping the lower ridge thereof to firmly remain in place.

After having explained the salient components of the Neuro-navigation system in accordance with the invention, the invention will now be further detailed by describing a typical operative treatment sequence.

On a patient requiring brain surgery firstly five landmark bases 92 are affixed to the skin surrounding the portions of the cranium to be opened. For referencing the anatomical data to a computer tomography five spherical aluminum landmark prominences 70 are inserted in the bases 92. The locations for attaching the landmarks are selected so that they experience minimum displacement during operative treatment, it being required that they are located as near as possible to the point of operative treatment whilst being spaced away from each other as far as possible. At least three landmarks need to be used, although making use of two additional landmarks endows the system with added accuracy and reliability.

Next, a computer tomography is made in which the portions to be operated on as well as the landmarks are mapped relative to each other.

Whilst the patient is being brought to surgery the CT data is stored on optical disks which are then brought to the computer unit 11 which reads the data for image display on the monitor 12. These images are section images in various planes as well as a three-dimensional image. The surgeon can plan his operation strategy according to these images. Whilst the anaesthetics of the patient are being prepared the position of the cameras 14 on the stand is calibrated, the surgeon using for this purpose a calibration rod 60 having two reflectors 61 and 62 and moving it in the viewing field of the cameras 14. By viewing roughly ten momentary positions of the reflectors 61 and 62 on the calibration rod 60 in brief spacings the system is able to "recognize" and memorize the camera position.

The head of the patient is then rendered unmovable in any direction on the operating table by a locating means. This is followed by replacing the spherical landmark prominences 70 by the partial spherical landmark prominences 80 provided with positioning funnels 83.

After sterilization the patient is covered with sterile cloths, these also concealing the landmarks 80. Covering may be done by means of conventionally cloths or by means of a transparent plastics film.

In the next step a reference adapter 50 is attached to the device locating the head of the patient. This reference adapter is identified by its unique reflector arrangement, its position as well as the position of its calibration point 57 being established by the Neuro-navigation system.

Using a pointer 20 known to the system and likewise identified, the surgeon is then able to access the five landmark prominences 80, i.e. by introducing in each case the tip 23 of the pointer 20 precisely into the tip of the funnel, which is the centerpoint of the ball 81. From the known data of the landmark prominences in each case, each of which is distinguishable, the system is able to identify each of the landmarks concerned within seconds and thus also to read the anatomical data of the patient from the computer tomography into its mapping system. The position of the tips of the neurosurgical instruments can now be displayed on the monitor 12 relative to the adapter, this applying also for any surgical instrument to which a reflector adapter 31 has been applied after calibration at the calibration point 57 of the reference adapter 50.

To precisely define the location at which an invasion needs to be made, the tip of a pointer, pointing to the scalp, can be virtually extended in length. The surgeon has a virtual view of the lesion to be operatively treated from the monitor output and is able to define in advance the optimum path of invasion from the likewise virtual extension in length of his instrument.

After the cranium has been opened at the position thus located a pincette 30 having a triple reflector adapter 31 attached thereto can be calibrated at the calibration point 57 of the reference adapter 50, i.e. the precise location of the pincette tip 35 is defined. Using this pincette 30 resection of the lesion can then be undertaken, the surgeon being able to trace the tip 35 of the pincette 30 at all times on the display 12.

Resection of the lesion can thus be carried out by this method in avoiding destruction of healthy tissue to a major degree. Furthermore, the operation can be implemented in a very short time. All instruments used can be moved cordlessly due to the application of passive reflectors, saving the surgeon from obstructions during the operation. In making use of triple reflector adapters he is able to employ the instruments he is used to. All of these factors may result in an overall improvement in the outcome of the operation.

What is claimed is:

1. An image-guided surgical system comprising at least one instrument that is tracked by a navigation system, and a calibration device tracked by the navigation system, the calibration device including a conical bowl terminating at a central calibration point for locating a tip of the instrument at a known location in the navigation system.

2. The image-guided surgical system of claim 1, wherein the calibration device includes an adapter that can be mounted to another device, and the conical bowl is part of the adapter.

3. The image-guided surgical system of claim 2, wherein the adapter has fixed thereto a plurality of reference markers that are trackable by the navigation system.

4. The image-guided surgical system of claim 3, wherein the reference markers are reflectors that are secured to the adapter in a characteristic arrangement.

5. The image-guided surgical system of claim 4, wherein the adapter has a center portion and three arms radiating from the center portion, the reference markers are fixed to the ends of the arms, and the conical bowl is located at the center portion.

6. The image-guided surgical system of claim 5, wherein the arms have different lengths and/or angular spacings.

7. The image-guided surgical system of claim 3, wherein the adapter has a center portion and three arms radiating from the center portion, the reference markers are fixed to the ends of the arms, and the conical bowl is located at the center portion.

8. The image-guided surgical system of claim 5, wherein the arms have different lengths and/or angular spacings.

9. The image-guided surgical system of claim 8, wherein the navigation system includes at least two mapping cameras and a computer unit connected to the cameras having a graphic display terminal.

10. The image-guided surgical system of claim 1, wherein the navigation system includes at least two mapping cameras and a computer unit connected to the cameras having a graphic display terminal.

11. The image-guided surgical system of claim 1, wherein the calibration device has fixed thereto a plurality of reference markers that are trackable by the navigation system.

12. The image-guided surgical system of claim 4, wherein the calibration device has a center portion and three arms radiating from the center portion, the reference markers are fixed to the ends of the arms, and the conical bowl is located at the center portion.

* * * * *